(12) United States Patent
Molesky (10) Patent No.: US 9,026,237 B2
(45) Date of Patent: May 5, 2015

(54) GENERATING AUDIO IMPRESSIONS OF DATA

(71) Applicant: Oracle International Corporation, Redwood Shores, CA (US)

(72) Inventor: Lory D. Molesky, Lexington, MA (US)

(73) Assignee: Oracle International Corporation, Redwood Shores, CA (US)

( * ) Notice: Subject to any disclaimer, the term of this patent is extended or adjusted under 35 U.S.C. 154(b) by 265 days.

(21) Appl. No.: 13/624,110

(22) Filed: Sep. 21, 2012

(65) Prior Publication Data

US 2014/0088741 A1      Mar. 27, 2014

(51) Int. Cl.
| | |
|---|---|
| *G09B 21/00* | (2006.01) |
| *A61F 9/08* | (2006.01) |
| *G06F 3/16* | (2006.01) |
| *G06F 17/30* | (2006.01) |
| *G10L 13/04* | (2013.01) |

(52) U.S. Cl.
CPC .............. *G09B 21/006* (2013.01); *G10L 13/043* (2013.01); *G06F 3/167* (2013.01); *A61F 9/08* (2013.01); *G06F 17/30056* (2013.01); *G06F 17/30569* (2013.01)

(58) Field of Classification Search
CPC ..... G10L 13/043; G09B 21/006; G06F 3/167; A61F 9/08
USPC ............ 700/94; 704/260, 263, 268, 271, 276; 715/716, 727, 729; 84/622, 627
See application file for complete search history.

(56) References Cited

U.S. PATENT DOCUMENTS

| | | | | |
|---|---|---|---|---|
| 5,287,120 | A | * | 2/1994 | Okada et al. .................. 345/163 |
| 5,461,399 | A | * | 10/1995 | Cragun ......................... 715/729 |
| 5,715,412 | A | * | 2/1998 | Aritsuka et al. ............... 715/729 |
| 2010/0134261 | A1 | * | 6/2010 | Heimendinger ........... 340/407.1 |

* cited by examiner

*Primary Examiner* — Jesse Elbin
(74) *Attorney, Agent, or Firm* — Miles & Stockbridge P.C.

(57) ABSTRACT

A system for generating audio impressions of data for a visually-impaired user. The system receives data that is displayable by a chart. The data comprises a plurality of values. The system generates an audio impression of the received data. The audio impression includes a first portion and a second portion. The first portion is based upon at least a first value of the received data. The second portion is based upon at least a second value of the received data. An audible difference between the first portion and the second portion reflects the magnitude of a difference between the first value and the second value.

23 Claims, 12 Drawing Sheets

GENERATING AUDIO IMPRESSIONS OF DATA

FIELD

One embodiment is directed generally to a computer system, and in particular to a computer system that generates an audio impression of data for a visually-impaired user.

BACKGROUND INFORMATION

Visual impairment is generally understood as vision loss to such a degree as to be considered a signification limitation of visual capability. A visually-impaired individual may be "partially sighted," "with low vision," "legally blind," or "totally blind," depending upon the degree of visual impairment. Also, depending upon the degree of visual impairment, a visually-impaired individual may require additional support or tools to perform the activities of daily life.

For example, a visually-impaired individual may utilize tactile or auditory feedback tools to assist in the performing of activities of daily life. Such tools may include speech-synthesis systems and systems using braille displays. These and other tools have enabled the visually-impaired to more effectively use mainstream computer applications. The availability of assistive technology for the visually-impaired has been increasing, and there have been increasing efforts to further develop assistive technologies that enable the visually-impaired to more effectively access information available on computer systems.

SUMMARY

One embodiment is a system for generating audio impressions of data for a visually-impaired user. The system receives data that is displayable by a chart. The data comprises a plurality of values. The system generates an audio impression of the received data. The audio impression includes a first portion and a second portion. The first portion is based upon at least a first value of the received data. The second portion is based upon at least a second value of the received data. An audible difference between the first portion and the second portion reflects the magnitude of a difference between the first value and the second value.

DETAILED DESCRIPTION

One embodiment is a system for generating audio impressions of data for the visually-impaired. The system converts visual representations of data (e.g., data that is displayable by a chart) into respective audio impressions. Each portion of the audio impression is generated in accordance with the magnitude of the value of the data for which the portion of audio impression represents. By listening to how an audio impression varies, a visually-impaired user can more readily ascertain the trends and shapes within the underlying data.

In previous methods for providing accessible interfaces to visually-impaired users, tools (such as screen readers) convert numerical values to spoken language. For example, in order to present information displayed on a chart to a visually-impaired user, the screen reader would first access a table of analog values that correspond to the values displayed by the chart. The screen reader would then read each of the values of the chart to the user via an audible voice output. For example, a screen reader first receives the value "100.1," next, converts the value into an audio equivalent, and then subsequently reads out the value to the user as "one-hundred point one."

However, these screen readers are often tedious to use because they provide a large amount of detailed data without providing a high-level picture or "feel" of the data. In order for a user to discern a trend in the data using a screen reader, the user needs to hear many numbers before the user is able to discern the trend. Therefore, visually-impaired users using screen readers often have difficulty perceiving overall trends or shapes of the displayed data.

In contrast with the previous approaches, embodiments of the present invention generate an audio impression that allows the visually impaired user to more readily perceive the shape of the data, and allows the user to more quickly receive and comprehend the information. Advantages provided by certain embodiments of the invention over the previous approaches are particularly evident when these embodiments are applied to charts that contain a large amount of associated data (e.g., charts that display hundreds of data points).

For example, suppose that a user wants to receive information from a simple line chart with a line (defined by (x,y) coordinates) that runs from (0,0) to (100, 15). In one embodiment, the system plays an audio impression of a pitch, lasting for a specified duration (e.g., a few seconds), that rises continuously from a low pitch to a high pitch. By listening to the audio impression, the visually impaired user can quickly recognize the data as being presented as a line chart with a positive slope.

Because these audio impressions allow the visually-impaired user to quickly gauge the shape of chart data, interfaces which implement embodiments of the invention may be considered to be closer to the ideal "equivalent interface" needed for Americans with Disabilities Act ("ADA") compliance.

Figure 1:
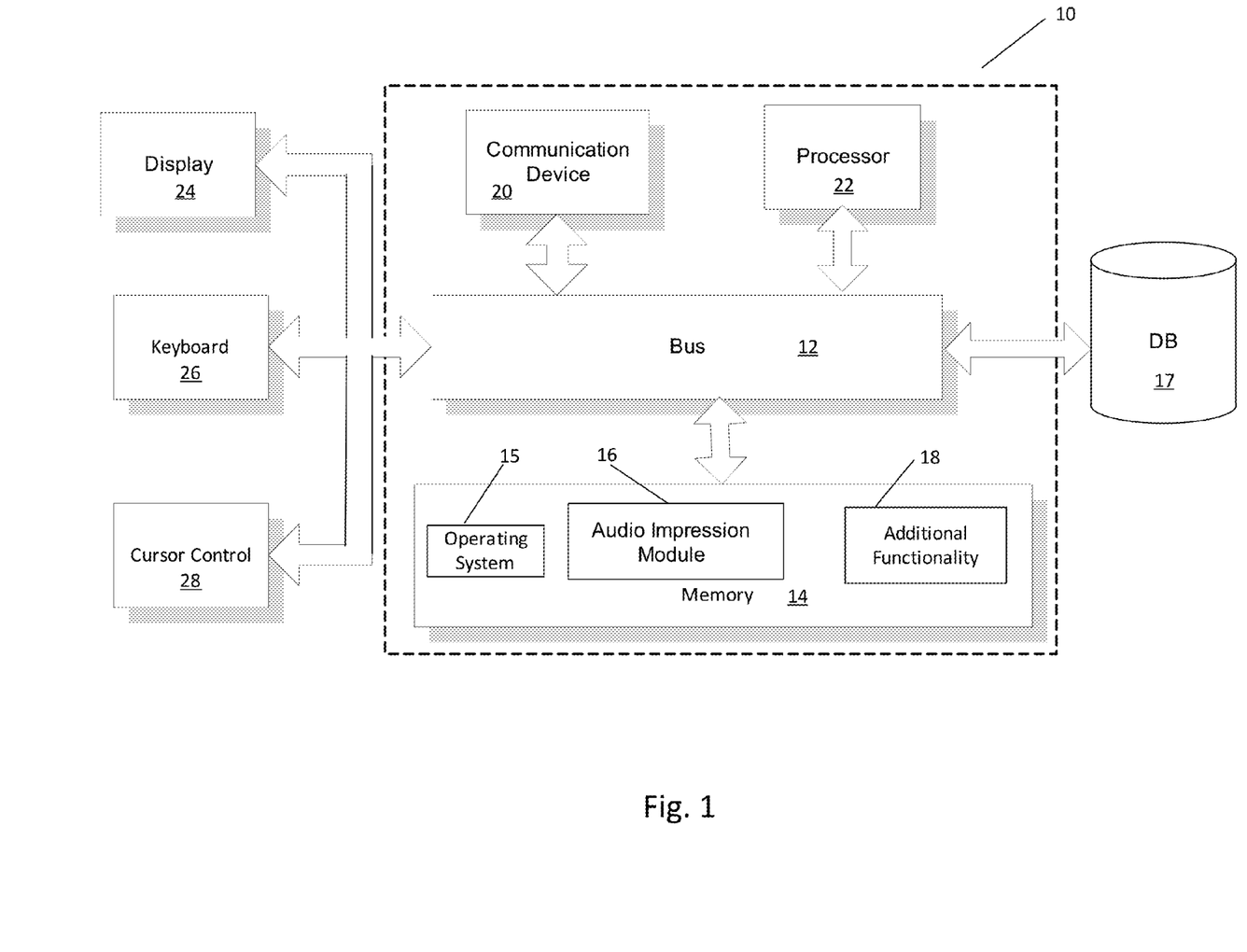
FIG. 1 is an overview block diagram of a computer system for generating audio impressions of data in accordance with an embodiment of the present invention.

FIG. 1 is an overview block diagram of a computer system 10 for generating audio impressions of data in accordance with an embodiment of the present invention. Although shown as a single system, the functionality of system 10 can be implemented as a distributed system. System 10 includes a bus 12 or other communication mechanism for communicating information, and a processor 22 coupled to bus 12 for processing information. Processor 22 may be any type of general or specific purpose processor. System 10 further includes a memory 14 for storing information and instructions to be executed by processor 22. Memory 14 can be comprised of any combination of random access memory ("RAM"), read only memory ("ROM"), static storage such as a magnetic or optical disk, or any other type of computer readable media. System 10 further includes a communication device 20, such as a network interface card, to provide access to a network. Therefore, a user may interface with system 10 directly, or remotely through a network or any other known method.

Computer readable media may be any available media that can be accessed by processor 22 and includes both volatile and nonvolatile media, removable and non-removable media, and communication media. Communication media may include computer readable instructions, data structures, program modules or other data in a modulated data signal such as a carrier wave or other transport mechanism and includes any information delivery media.

Processor 22 may be further coupled via bus 12 to a display 24, such as a Liquid Crystal Display ("LCD"). A keyboard 26 and a cursor control device 28, such as a computer mouse, may be further coupled to bus 12 to enable a user to interface with system 10.

In one embodiment, memory 14 stores software modules that provide functionality when executed by processor 22. The modules include an operating system 15 that provides operating system functionality for system 10. The modules further include audio impression module 16 for an audio impression generating system that allows a user to receive audio impressions based upon data displayed by a chart, as disclosed in more detail below. System 10 can be part of a larger system. Therefore, system 10 will typically include one or more additional functional modules 18 to include additional functionality, such as data processing functionality for generating the data that is used to create the audio impressions. A database 17 is coupled to bus 12 to store data used with modules 16 and 18.

Figure 2:
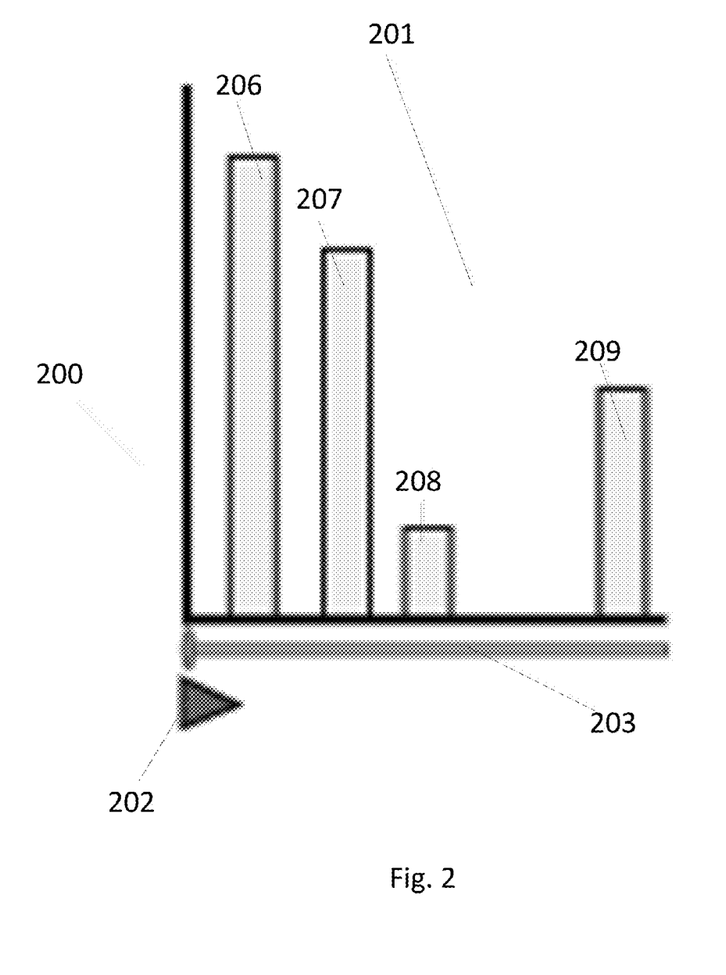
FIG. 2 is a screen shot of an interface that generates an audio impression of data displayed by a chart in accordance with one embodiment.

FIG. 2 is a screen shot of an interface 200 that generates an audio impression of data displayed by a chart 201 in accordance with one embodiment. Interface 200 includes at least one button 202 that may be activated to begin playing of an audio impression. Button 202 is positioned near chart 201. Interface 200 may also include a time marker 203 as part of interface 200. Time marker 203 serves to indicate which portion of the audio impression is currently being played. Interface 200 may also include other buttons and elements that are typically found on an interface of an audio player.

Upon activation of button 202 by the user, an audio impression corresponding to the values (i.e., values 206, 207, 208, and 209) of chart 201 is played. Each of the values 206, 207, 208, and 209 is converted/mapped to a portion of the audio impression. In one embodiment, silent gaps are provided in the audio impression to allow the user to differentiate between values 206, 207, 208, and 209, when the audio impression is being played.

In one embodiment, data represented as a continuous function is expressed by an audio impression including continuous pitch changes, while data represented as a step function is expressed by an audio impression including stepwise pitch changes.

Figure 3:
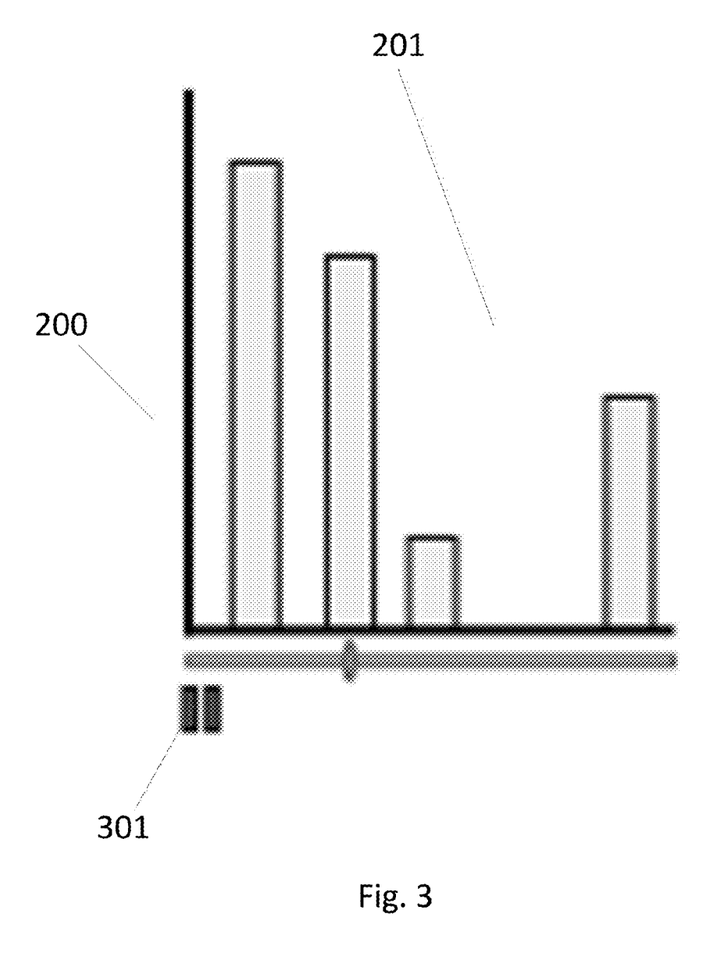
FIG. 3 is a screen shot of an interface that is playing an audio impression of data displayed by the chart of FIG. 2 in accordance with one embodiment.

FIG. 3 is a screen shot of an interface 200 that is playing an audio impression of data displayed by the chart 201 of FIG. 2 in accordance with one embodiment. While an audio impression corresponding to the chart data is being played, the triangle "play button" is replaced by a "pause button" 301. The user may pause the playing of the audio impression by activating pause button 301.

Figure 4:
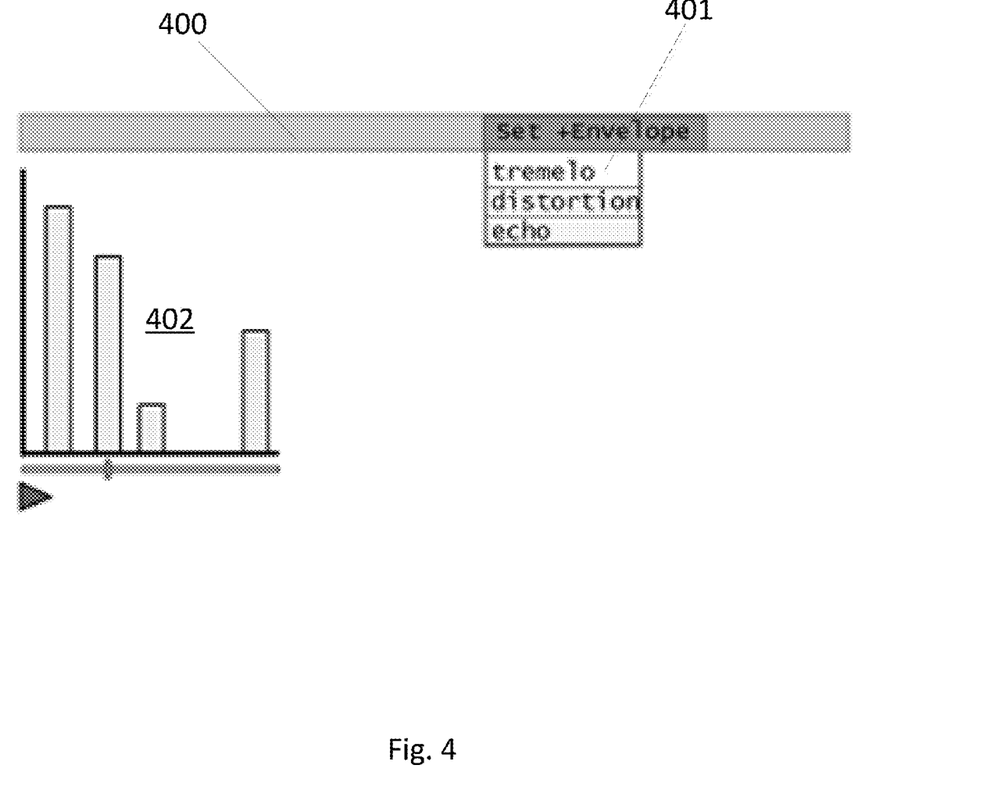
FIG. 4 is a screen shot of an interface that allows a user to select different envelope effects for playing an audio impression of data displayed by a chart in accordance with one embodiment.

FIG. 4 is a screen shot of an interface 400 that allows a user to select different envelope effects 401 for playing an audio impression of data displayed by a chart 402 in accordance with one embodiment. Additionally, interface 400 may provide different envelope options for expressing positive data values, as compared to negative data values, and as compared to data values that are zero. An envelope determines how a signal or sound changes over its period of existence, and includes, at least, the attack, sustain, and delay of a sound. For example, a particular envelope may add distortion effects to sound.

Figure 5:
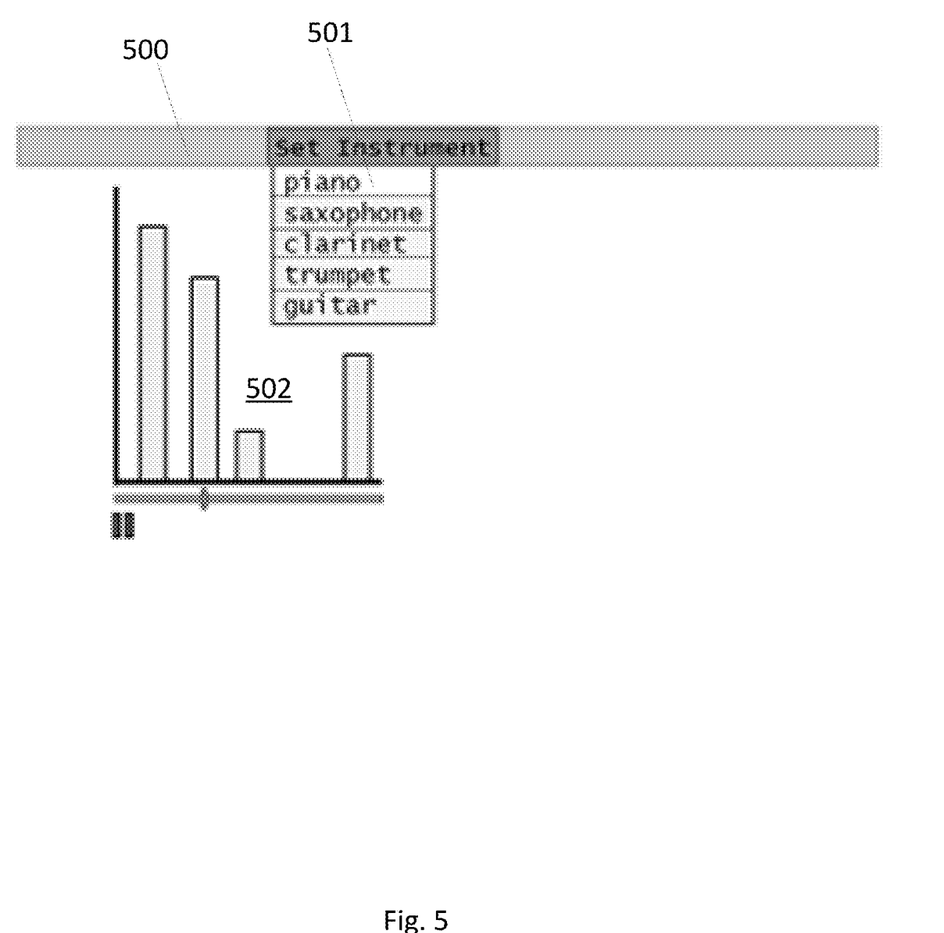
FIG. 5 is a screen shot of an interface that allows a user to select different instruments for playing an audio impression of data displayed by a chart in accordance with one embodiment.

FIG. 5 is a screen shot of an interface 500 that allows a user to select different instruments 501 for playing an audio impression of data displayed by a chart 502 in accordance with one embodiment. As described in further detail below, a chart may include data that relates to multiple, separate series. With these charts that include multiple series of data, interface 500 allows the user to change the instrument settings for each series.

In addition to allowing a user to select different envelope effects and different instruments for playing audio impressions of data, another embodiment allows a user to select a desired frequency range for playing audio impressions of data.

Figure 6:
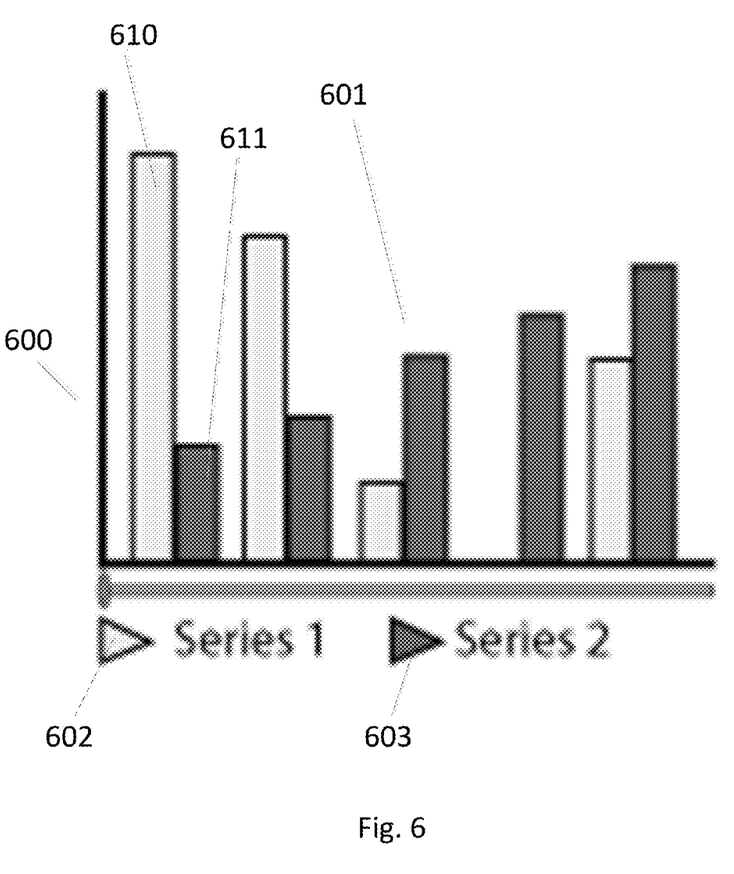
FIG. 6 is a screen shot of an interface that allows a user to play different audio impressions corresponding to separate series of data displayed by a chart in accordance with one embodiment.

FIG. 6 is a screen shot of an interface 600 that allows a user to play different audio impressions corresponding to separate series of data displayed by a chart 601 in accordance with one embodiment. Each of series 1 (corresponding to the white bar chart data, such as data 610) and series 2 (corresponding to the shaded bar chart data, such as data 611) of the data displayed by chart 601 is assigned a different instrument. For example, the audio impression corresponding to series 1 could be assigned to output piano sounds, while the audio impression corresponding to series 2 could be assigned to output saxophone sounds. The legend of chart 600 can include separate individual play buttons (buttons 602 and 603) associated with each individual series. Each of buttons 602 and 603 can be used to play each individual series in multi-series chart 601. In another embodiment, a "play all" button allows a user to play all audio impressions at the same time. Although FIG. 6 shows an embodiment having two series, other embodiments may have more than two series.

The play/pause buttons and text alignment associated with each series may appear similar to a legend for each series. Thus, colored symbols that are typically used for identifying different series within a legend can be augmented or replaced by colored pause and play buttons.

Figure 7:
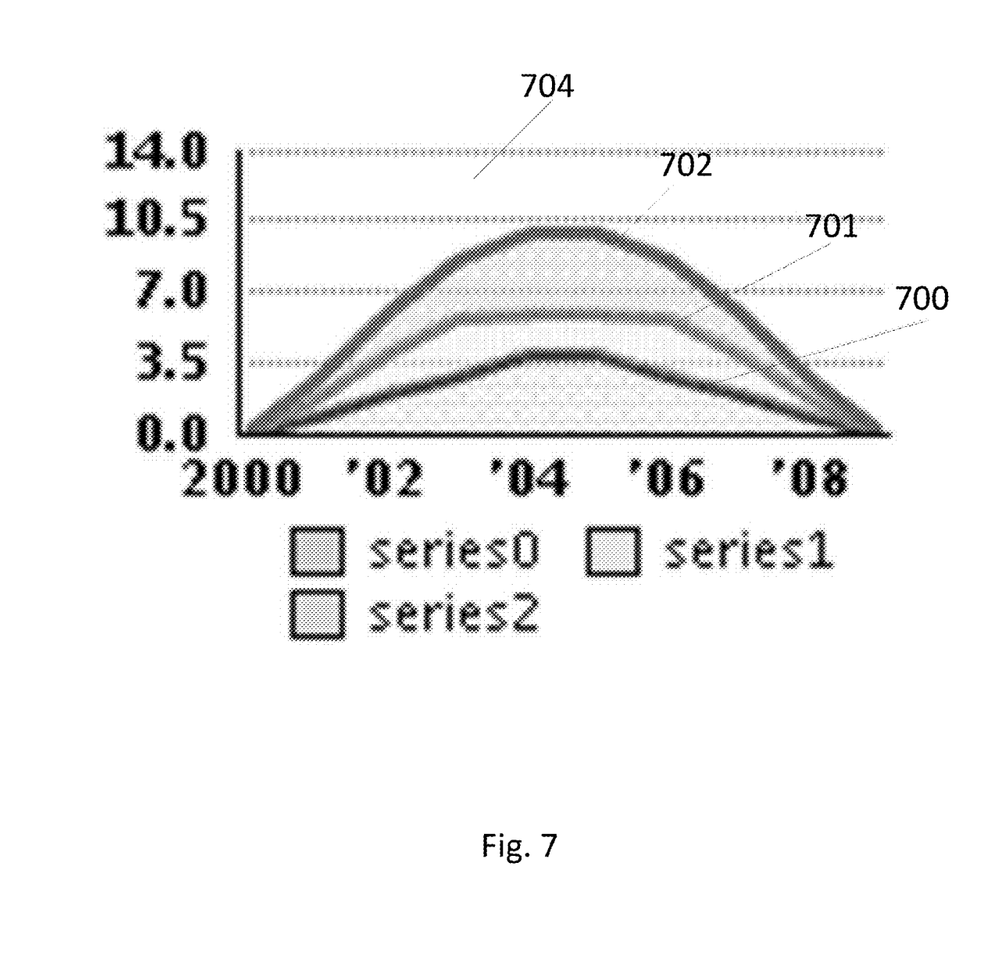
FIG. 7 illustrates one example of chart data that may be expressed by audio impressions in accordance with one embodiment.

FIG. 7 illustrates one example of chart data that may be expressed by audio impressions in accordance with one embodiment. For chart data with multiple, separate series (lines 700, 701, and 702 in a line chart 704), multiple instruments could be used to express the multiple lines. In FIG. 7, series 0 corresponds to line 700, series 1 corresponds to line 701, and series 2 corresponds to line 702. For example, the system may express series 0 as piano sounds, series 1 as trumpet sounds, and series 2 as saxophone sounds. Further, each series could be played separately or concurrently.

Figure 8:
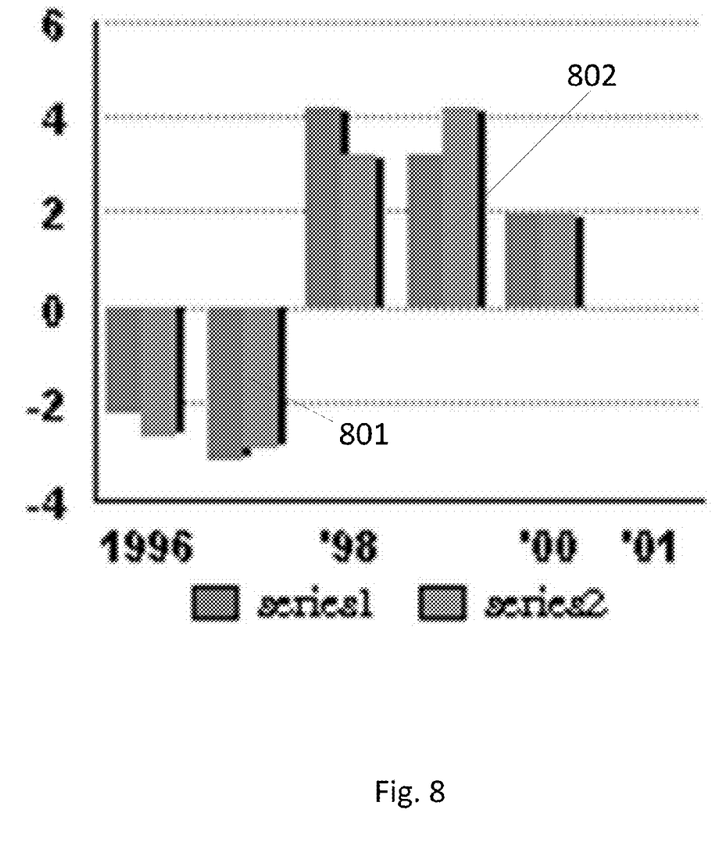
FIG. 8 illustrates a second example of chart data that may be expressed by audio impressions in accordance with one embodiment.

FIG. 8 illustrates a second example of chart data that may be expressed by audio impressions in accordance with one embodiment. Chart data with negative values 801 could be associated with a distinguishable envelope change, such as with a vibrato effect, or tremolo effect, for example, compared to the positive values 802. In another embodiment, chart data with negative values 801 could be associated with a different instrument, compared to positive values 802.

Figure 9:
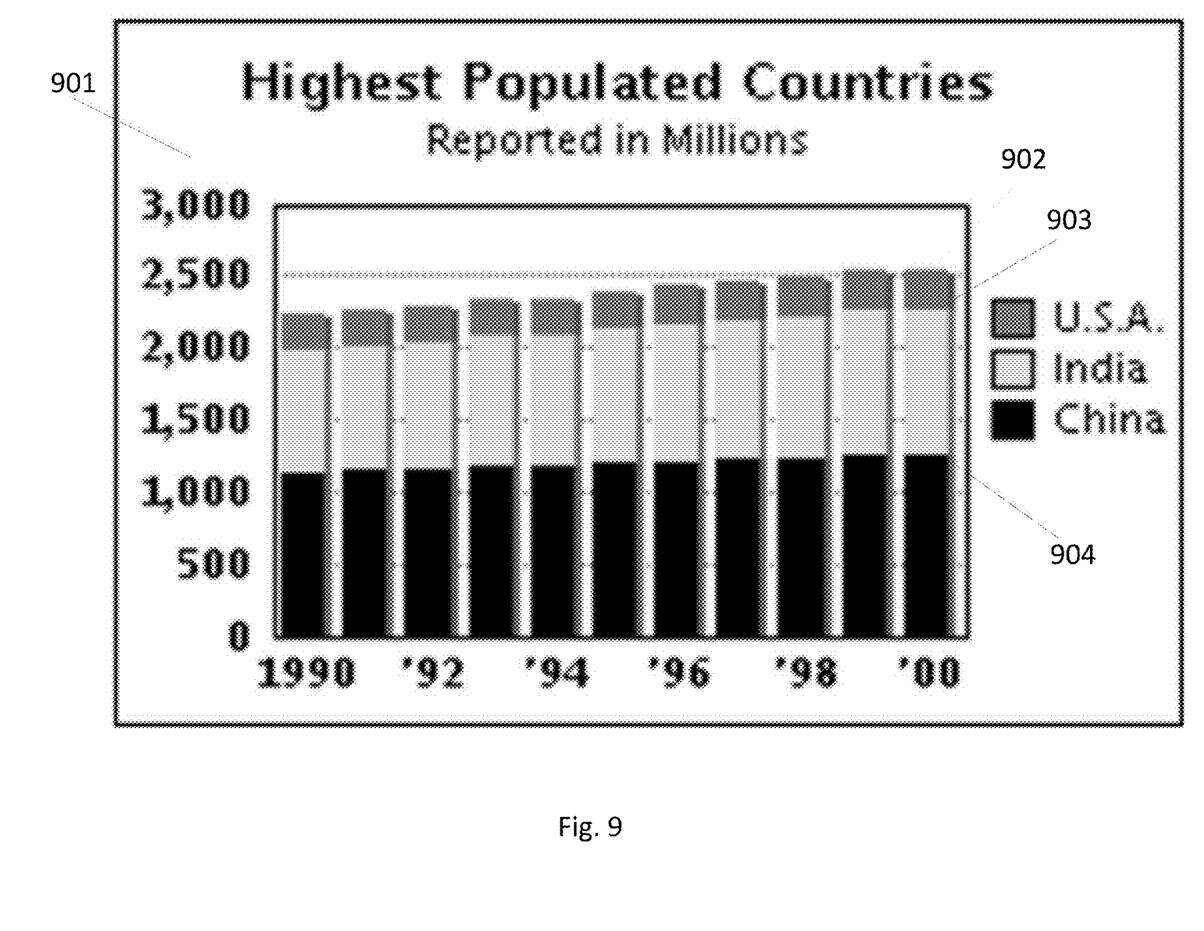
FIG. 9 illustrates a third example of chart data that may be expressed by audio impressions in accordance with one embodiment.

FIG. 9 illustrates a third example of chart data that may be expressed by audio impressions in accordance with one embodiment. The chart 901 of FIG. 9 is commonly referred to as a stacked bar chart. To express the stacked bar chart data of chart 901, certain embodiments may play two different pitches (at different times or at the same time), with one pitch corresponding to a lower boundary value and the other pitch corresponding to a higher boundary value. For example, to express a lower boundary 904 and an upper boundary 903 of "India" within bar 902, one pitch would correspond to lower boundary 904 and another pitch would correspond to upper boundary 903. Alternatively, certain embodiments of the invention may also play a pitch corresponding to the value of the relative difference between lower boundary value 904 and upper boundary value 903.

Figure 10:
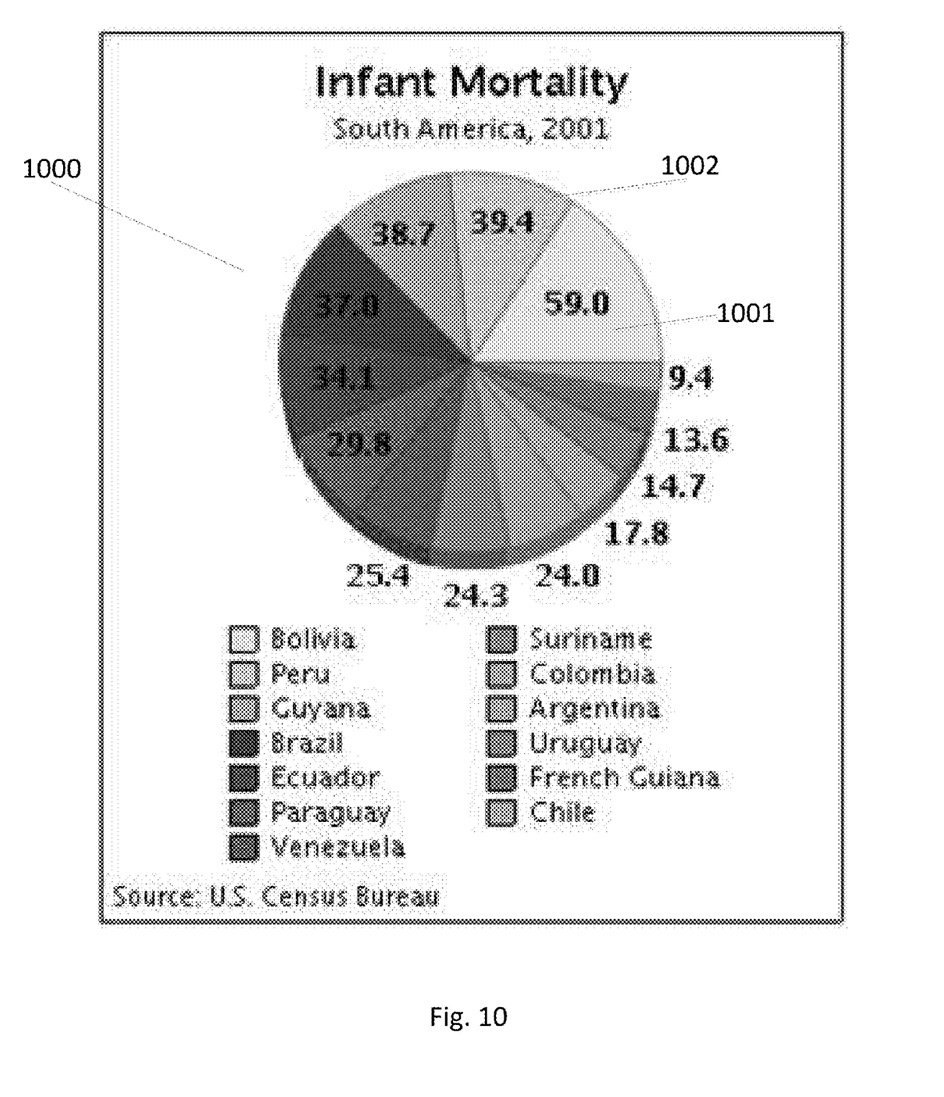
FIG. 10 illustrates a fourth example of chart data that may be expressed by audio impressions in accordance with one embodiment.

FIG. 10 illustrates a fourth example of chart data that may be expressed by audio impressions in accordance with one embodiment. Chart 1000 is commonly referred to as a pie chart. To express the chart data of pie chart 1000, certain embodiments may play audio impressions corresponding to magnitudes of values of the pieces of pie chart 1000. For example, to express the data value corresponding to pie piece 1001, an audio impression corresponding to the value "59.0" is played. To express the data value corresponding to pie piece 1002, an audio impression corresponding to the value "39.4" is played.

Figure 11:
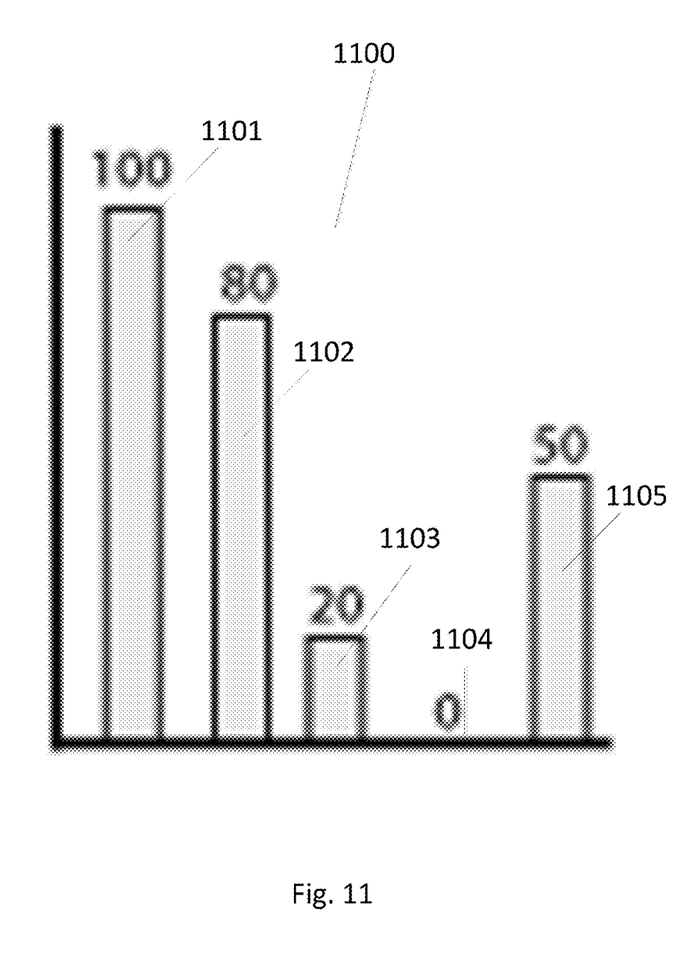
FIG. 11 illustrates a process of frequency mapping in accordance with one embodiment.

FIG. 11 illustrates a process of frequency mapping in accordance with one embodiment. In this example, data values (values 1101, 1102, 1103, 1104, and 1105) of chart 1100 are mapped to different frequencies. In one embodiment, the magnitude of data values 1101, 1102, 1103, 1104, and 1105 are mapped to different frequencies according to a non-linear scale (e.g. a logarithmic scale, for example). For example, one possible function for determining an appropriate frequency for a given magnitude of data value is provided as follows:

$$\text{Frequency} = 440 \times 2^{((n \times m)/12)} \quad (1)$$

The term "n" is dependent upon the desired octave range between the lower limit frequency and the upper limit frequency to be played. For example, suppose a user decides to set a one octave range (i.e., a range of 440 Hz) between the lower limit frequency (e.g., 440 Hz) and the upper limit frequency (e.g., 880 Hz) to be played. In this case, n would be set as "12." On the other hand, suppose a user decides to set a three octave range (i.e., a range of 1320 Hz) between the lower limit frequency (e.g., 440 Hz) and the upper limit frequency (e.g., 1760 Hz) to be played. In this second case, n would be set as "24." The term "n" can be modified in accordance to any desired octave range.

The term "m" corresponds to a magnitude of a data value of chart 1100 as expressed as a percentage of a magnitude of the total possible numerical range of the data values of chart 1100. For example, suppose that the user would like to set a one octave range (i.e., 440 Hz) between the lower limit frequency and the upper limit frequency to be played. As described above, n would be set as "12." Further, suppose that the data values of chart 1100 can range anywhere between "0" and "100." Bar 1102 of chart 1100 would have an "m" value of "0.8," corresponding to (magnitude data value of 80/magnitude of possible numerical range of 100). As such, bar 1102 (having a data value of 80) would be expressed as an audio impression with a frequency equivalent to 776.1 Hz. For reference purposes, $776.1 = 440 \times 2^{((12 \times 0.8)/12)}$ On the other hand, bar 1103 (having a data value of 20) would be expressed as an audio impression with a frequency equivalent to 505.4 Hz. For reference purposes, $505.4 = 440 \times 2^{((12 \times 0.2)/12)}$ Bar 1101 (having a data value of 100) would be expressed as an audio impression with a frequency equivalent to 880 Hz. For reference purposes, $880 = 440 \times 2^{((12 \times 1)/12)}$ Certain embodiments may also determine a relative difference between each data value compared to a baseline value. These relative differences may be mapped as different audio impression frequencies. Given a set of data values (e.g., 100, 100.1, 100.3, and 100.15), a baseline value (e.g., 100) may be used in order to more clearly differentiate between the data values. The relative differences (e.g., 0, 0.1, 0.3, and 0.15) between each data value compared to the baseline value may then be mapped as different audio impression frequencies. The baseline value may be equal to or approximately equal to one of the data values. Certain embodiments may comprise an interface that allows a user to toggle between mapping the magnitudes of the data values themselves and/or mapping the relative differences between the data values and a baseline value. In addition to mapping numerical data values to different audio impression frequencies, certain embodiments may also map character data values to different audio impression frequencies.

Figure 12:
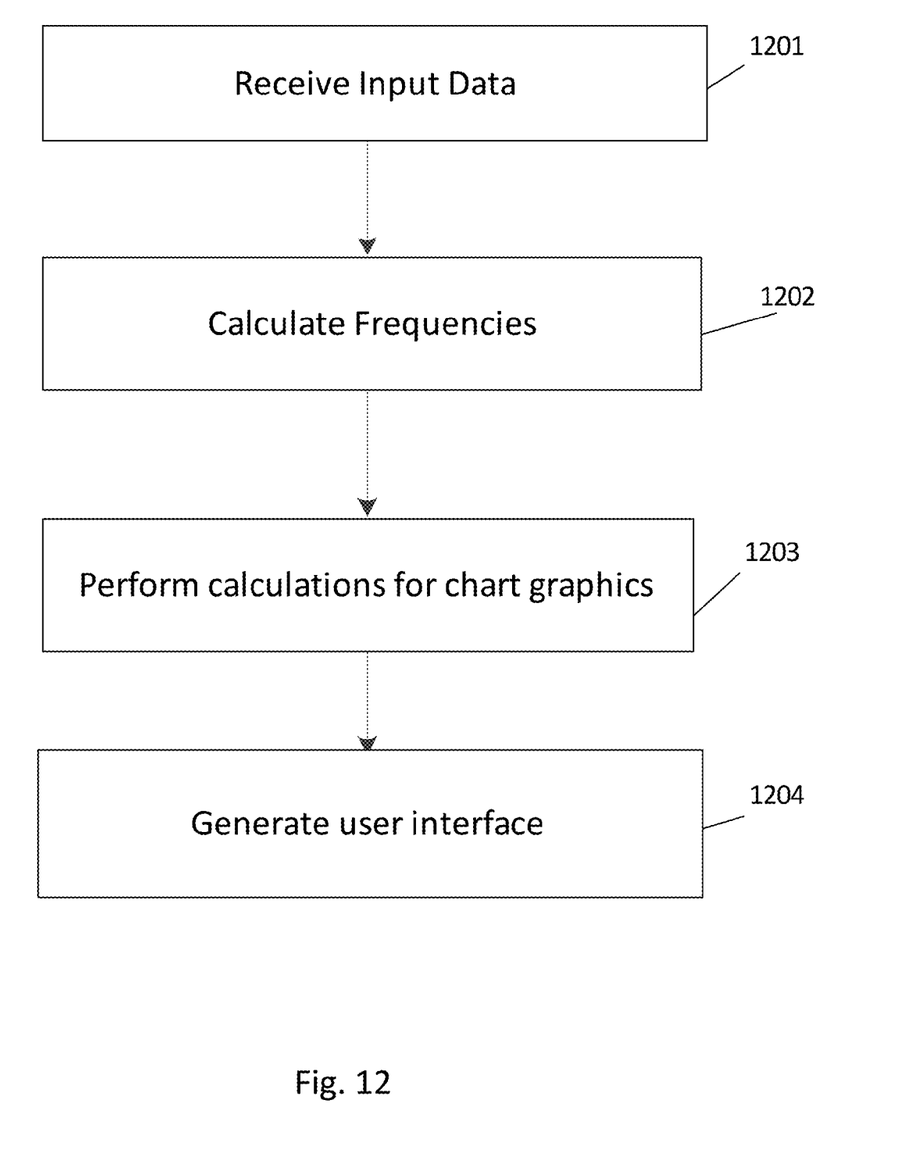
FIG. 12 is a flow diagram of the functionality of the audio impression module of FIG. 1 in accordance with one embodiment.

FIG. 12 is a flow diagram of the functionality of the audio impression module 16 of FIG. 1 in accordance with one embodiment. In one embodiment, the functionality of the flow diagram of FIG. 12 is implemented by software stored in memory or other computer readable or tangible medium, and executed by a processor. In other embodiments, the functionality may be performed by hardware (e.g., through the use of an application specific integrated circuit ("ASIC"), a programmable gate array ("PGA"), a field programmable gate array ("FPGA"), etc.), or any combination of hardware and software.

At 1201, the system receives data, such as chart data, for example, as input. As described above, in one embodiment, the chart data may be in the form of (x,y) coordinate pairs. The x axis may represent time while the y axis may represent the numerical magnitude values of the data. The system may receive global chart data, such as the chart title, series names, and legend positioning constraints, for example.

In certain embodiments, at 1201, the system optionally receives a frequency mapping function (such as equation (1), for example), a frequency mapping range, instrument mappings, or envelope mappings. These additional inputs have appropriate default values, but these default values can be changed via configuration files or via interaction by the user (such as by making selection 401 as shown in FIG. 4, for example).

At 1202, for each chart coordinate, frequencies (such as pitch frequencies, for example) are then calculated (as shown by the process illustrated by FIG. 11, for example). In one embodiment, data values along the y axis of a chart are converted into an audio pitch reflecting the magnitudes of the data values. For example, the greater the magnitude of the data value, the higher the audio pitch associated with the data value. For each data value, the x value would map to a point in time within the audio impression, and the y value would map to a pitch. As such, an audio impression representing the set of data is produced. In another embodiment, the produced audio impression is encoded into a standard audio format, such as mpeg or .wav, and may be played with a standard audio player.

At 1203, chart graphics are calculated. The graphics of the chart include, but are not limited to, the graphical representations of the displayed data, chart labels, and chart legends (as shown in FIG. 6, for example).

At 1204, the chart and its user interface are rendered for the user. In one embodiment, as provided by many user interfaces accessible to visually-impaired users, each mouse-driven operation has an associated keyboard equivalent. For example, the functions of the rendered user interface are associated with keyboard bindings which allow a visually-impaired user to play and to pause audio impressions, among other functions, using only the keyboard.

As described above, certain embodiments are directed to a system for generating an audio impression of data for the visually-impaired. Certain embodiments provide methods for converting visual representations of data into respective audio impressions. Each portion of the audio impression is generated in accordance with the value of the data for which the portion of audio impression represents. The generated audio impressions allow a visually impaired user to perceive the shape of the data. As such, the present system generates an audio impression of data that allows the user to more quickly receive and comprehend the information.

Several embodiments are specifically illustrated and/or described herein. However, it will be appreciated that modifications and variations of the disclosed embodiments are covered by the above teachings and within the purview of the appended claims without departing from the spirit and intended scope of the invention.

What is claimed is:

1. A non-transitory computer readable medium having instructions stored thereon that, when executed by a processor, cause the processor to generate audio impressions of data for a visually-impaired user, the generating comprising:
    receiving data that is displayable by a chart, the chart having an x-axis and a y-axis, the data comprising a plurality of values in a first series; and
    producing an audio impression of the first series of the received data, wherein the audio impression includes at least a first portion and a second portion, the first portion is based upon at least a first y-axis value of the first series of the received data, the second portion is based upon at least a second y-axis value of the first series of the received data, and an audible difference between the first portion and the second portion reflects the magnitude of a difference between the first y-axis value and the second y-axis value of the first series,
    wherein a time difference between the first and second portions reflects a magnitude of a difference between a first x-axis value associated with the first y-axis value and a second x-axis value associated with the second y-axis value.

2. The non-transitory computer readable medium of claim 1, wherein the generating further comprises providing a user interface that allows the user to select from a list of different envelopes to be applied to the audio impression, and the selected envelope is applied to the audio impression.

3. The non-transitory computer readable medium of claim 1, wherein the generating further comprises providing a user interface that allows the user to select from a list of different instruments for the first series, and the audio impression of the first series is played according to the sounds of the selected instrument.

4. The non-transitory computer readable medium of claim 1, the generating further comprising:
    producing additional audio impressions from the received data, wherein each audio impression corresponds to a separate series displayable by the chart; and
    providing a user interface that allows the user to select from a list of different instruments for each series, and the audio impression of each series is played according to the sounds of the selected instrument.

5. The non-transitory computer readable medium of claim 1, wherein producing the audio impression of the first series of the received data includes calculating audible frequencies (f) in accordance with $f=440*2^{((n\times m)/12)}$, where n is an octave range selected by the user and m corresponds to the magnitude of the data value within the first series.

6. The computer readable medium of claim 1, further comprising providing an interface that allows the user to play the audio impression of the first series of the received data and displays a representation of the chart with a time marker, a location of the time marker indicating a location of the data within the chart that corresponds to a portion of the audible impression played at that time.

7. The non-transitory computer readable medium of claim 1, wherein the first portion is based upon at least a difference between the first y-axis value compared to a baseline value, and the second portion is based upon at least a difference between the second y-axis value compared to the baseline value.

8. The non-transitory computer readable medium of claim 1, wherein the audio impression continuously changes pitch to correspond to changes in the first series that are continuous and changes pitch in steps to correspond to changes in the first series that are step-wise.

9. The non-transitory computer readable medium of claim 1, wherein a silent period in the audio impression indicates a separation along the x-axis between sequential data points in the first series.

10. The non-transitory computer readable medium of claim 1, wherein at least one of distortion, vibrato, or tremolo in the audio impression indicates a negative y-axis value of the first series.

11. A method for generating audio impressions of data for a visually-impaired user, the method comprising:
    receiving data that is displayable by a chart, the chart having an x-axis and a y-axis, the data comprising a plurality of values in a first series;
    producing an audio impression of the first series of the received data, wherein the audio impression includes at least a first portion and a second portion, the first portion is based upon at least a first y-axis value of the first series of the received data, the second portion is based upon at least a second y-axis value of the first series of the received data, and an audible difference between the first portion and the second portion reflects the magnitude of a difference between the first y-axis value and the second y-axis value of the first series,
    wherein a time difference between the first and second portions reflects a magnitude of a difference between a first x-axis value associated with the first y-axis value and a second x-axis value associated with the second y-axis value.

12. The method of claim 11, further comprising providing a user interface that allows the user to select from a list of different envelopes to be applied to the audio impression, and the selected envelope is applied to the audio impression.

13. The method of claim 11, further comprising providing a user interface that allows the user to select from a list of different instruments for the first series, and the audio impression of the first series is played according to the sounds of the selected instrument.

14. The method of claim 11, the method further comprising:
producing additional audio impressions from the received data, wherein each audio impression corresponds to a separate series displayable by the chart; and
providing a user interface that allows the user to select from a list of different instruments for each series, and the audio impression of each series is played according to the sounds of the selected instrument.

15. The method of claim 11, wherein producing the audio impression of the first series of the received data includes calculating audible frequencies (f) in accordance with $f=440*2^{((n \times m)/12)}$, where n is an octave range selected by the user and m corresponds to the magnitude of the data value within the first series.

16. The method of claim 11, further comprising providing an interface that allows the user to play the audio impression of the first series of the received data and displays a representation of the chart with a time marker, a location of the time marker indicating a location of the data within the chart that corresponds to a portion of the audible impression played at that time.

17. The method of claim 11, wherein the first portion is based upon at least a difference between the first y-axis value compared to a baseline value, and the second portion is based upon at least a difference between the second y-axis value compared to the baseline value.

18. A system for generating audio impressions of data for a visually-impaired user, the system comprising:
a processor;
a memory coupled to the processor;
a receiving module that receives data that is displayable by a chart, the chart having an x-axis and a y-axis, the data comprising a plurality of values in a first series; and
a first generating module that produces an audio impression of the first series of the received data, wherein the audio impression includes at least a first portion and a second portion, the first portion is based upon at least a first y-axis value of the first series of the received data, the second portion is based upon at least a second y-axis value of the first series of the received data, and an audible difference between the first portion and the second portion reflects the magnitude of a difference between the first axis value and the second y-axis value of the first series,
wherein a time difference between the first and second portions reflects a magnitude of a difference between a first x-axis value associated with the first y-axis value and a second x-axis value associated with the second y-axis value.

19. The system of claim 18, further comprising an interface module that provides a user interface, which allows the user to select from a list of different envelopes to be applied to the audio impression, and the selected envelope is applied to the audio impression.

20. The system of claim 18, further comprising an interface module that provides a user interface, which allows the user to select from a list of different instruments for the first series, and the audio impression of the first series is played according to the sounds of the selected instrument.

21. The system of claim 18, the system further comprising:
a second generating module that produces additional audio impressions from the received data, wherein each audio impression corresponds to a separate series displayable by the chart; and
an interface module that provides a user interface, which allows the user to select from a list of different instruments for each series, and the audio impression of each series is played according to the sounds of the selected instrument.

22. The system of claim 18, wherein the first generating module is configured to produce the audio impression of the received data by calculating audible frequencies in accordance with $f=440*2^{((n-m)/12)}$, where n is an octave range selected by the user and m corresponds to the magnitude of the data value within the first series.

23. The system of claim 18, further comprising an interface module that provides an interface that allows the user to play the audio impression of the first series of the received data and displays a representation of the chart with a time marker, a location of the time marker indicating a location of the data within the chart that corresponds to a portion of the audible impression played at that time.

* * * * *

UNITED STATES PATENT AND TRADEMARK OFFICE
CERTIFICATE OF CORRECTION

PATENT NO. : 9,026,237 B2  
APPLICATION NO. : 13/624110  
DATED : April 28, 2015  
INVENTOR(S) : Molesky Page 1 of 1

It is certified that error appears in the above-identified patent and that said Letters Patent is hereby corrected as shown below:

In the specification

Column 6, line 9, delete "$776.1=440\times2^{((12\times0.8)/12)}$" and insert -- $776.1=440\times2^{((12\times0.8)/12)}$. --, therefor.

Column 6, lines 12-13, delete "$505.4=440\times2^{((12\times0.2)/12)}$" and insert -- $505.4=440\times2^{((12\times0.2)/12)}$. --, therefor.

Column 6, line 16, delete "$880=440\times2^{((12\times1)/12)}$" and insert -- $880=440\times2^{((12\times1)/12)}$. --, therefor.

In the claims

Column 8, line 20, Claim 6, delete "computer" and insert -- non-transitory computer --, therefor.

Column 10, line 5, Claim 18, delete "axis" and insert -- y-axis --, therefor.

Column 10, line 36, Claim 22, delete "$f=440*2^{((n-m)/12)}$," and insert -- $f=440*2^{((n\times m)/12)}$, --, therefor.

Signed and Sealed this  
Ninth Day of February, 2016

Michelle K. Lee  
*Director of the United States Patent and Trademark Office*